United States Patent
Ichim et al.

(10) Patent No.: US 10,030,227 B2
(45) Date of Patent: Jul. 24, 2018

(54) CANINE AUTOLOGOUS IMMUNOTHERAPY USING DENDRITIC CELL INDUCED CANCER KILLING IMMUNOCYTES

(71) Applicant: Zander Therapeutics, Inc., Carson City, NV (US)

(72) Inventors: Thomas Ichim, San Diego, CA (US); David Koos, La Mesa, CA (US)

( * ) Notice: Subject to any disclaimer, the term of this patent is extended or adjusted under 35 U.S.C. 154(b) by 0 days.

(21) Appl. No.: 15/225,484

(22) Filed: Aug. 1, 2016

(65) Prior Publication Data

US 2017/0029775 A1    Feb. 2, 2017

Related U.S. Application Data

(60) Provisional application No. 62/199,256, filed on Jul. 31, 2015.

(51) Int. Cl.
*C12N 5/0784*    (2010.01)
*A61K 39/00*    (2006.01)

(52) U.S. Cl.
CPC ........ *C12N 5/0639* (2013.01); *A61K 39/0011* (2013.01); *A61K 2039/5154* (2013.01); *A61K 2039/552* (2013.01); *C12N 2501/22* (2013.01); *C12N 2501/2302* (2013.01); *C12N 2501/2304* (2013.01); *C12N 2501/51* (2013.01); *C12N 2501/515* (2013.01); *C12N 2502/1114* (2013.01); *C12N 2506/115* (2013.01)

(58) Field of Classification Search
CPC .................................................. C12N 5/0639
See application file for complete search history.

*Primary Examiner* — Bin Shen
(74) *Attorney, Agent, or Firm* — Baumgartner Patent Law; Marc Baumgartner

(57) ABSTRACT

Described are compositions of matter, protocols, and treatment means for induction of immune mediated killing in dogs suffering from cancer. The invention provides means of extracting peripheral blood from a canine patient, expanding immunocytes capable of killing cancer cells in vitro, and re-administering said immunocytes into a patient in need of therapy. In one embodiment, immunocytes expanded are T cells possessing tumor cytotoxic activity induced by stimulation of NKG2D.

16 Claims, No Drawings

CANINE AUTOLOGOUS IMMUNOTHERAPY USING DENDRITIC CELL INDUCED CANCER KILLING IMMUNOCYTES

CROSS-REFERENCE TO RELATED APPLICATIONS

The present application claims priority to U.S. Provisional Application No. 62/199,256 filed Jul. 31, 2015, which is hereby incorporated in its entirety including all tables, figures, and claims.

FIELD OF THE INVENTION

The invention pertains to the field of cancer immunotherapy, more specifically, the field pertains to the utilization of cancer immunotherapy in canine patients, more specifically the invention relates to generation of potent cytotoxic cells through the utilization of antigen presenting cells as stimulators.

BACKGROUND OF THE INVENTION

Dendritic cells (DC) were originally identified by Ralph Steinman as bone marrow derived professional antigen presenting cells, being the only cell of the immune system capable of activating naïve T cells [1]. Subsequent studies have shown that DC act as a critical bridge between the innate immune system, which is constantly patrolling for various "danger" signals such as toll like receptor (TLR) agonists that are associated with tissue injury or pathogenic threat. In contrast to other antigen presenting cells such as the macrophage or the B cell, DC exhibit magnitudes of higher ability to stimulate T cell responses both in antigen specific systems, as well as in polyclonal experiments such as in mixed lymphocyte reaction [2]. It is known that in peripheral tissues (outside of lymph nodes), DCs capture antigens through several complementary mechanisms including phagocytosis and receptor mediated endocytosis. Immature DC are known to possess high degree of phagocytic activity and low levels of antigen presenting activity. Normally, DCs in peripheral tissues are immature. These immature DCs have the ability to efficiently capture antigens; they can accumulate MHC class II molecules in the late endosome-lysosomal compartment; they can express low levels of co-stimulatory molecules; they can express a unique set of chemokine receptors (such as CCR7) that allow their migration to lymphoid tissues; and they have a limited capacity for secreting cytokines [3].

Once DC are activated, by a stimulatory signal such as a toll like receptor agonist, phagocytic activity decreases and the DC then migrate into the draining lymph nodes through the afferent lymphatics. During the trafficking process, DC degrade ingested proteins into peptides that bind to both MHC class I molecules and MHC class II molecules. This allows the DC to: a) perform cross presentation in that they ingest exogenous antigens but present peptides in the MHC I pathway; and b) activate both CD8 (via MHC I) and CD4 (via MHC II). Interestingly, lipid antigens are processed via different pathways and are loaded onto non-classical MHC molecules of the CD1 family [4]. DCs promptly respond to environmental signals and differentiate into mature DCs that can efficiently launch immune responses. As stated above, maturation is associated with the downregulation of antigen-capture activity, the increased expression of surface MHC class II molecules and costimulatory molecules, the ability to secrete cytokines as well as the acquisition of CCR7, which allows migration of the DC into the draining lymph node. The ligation of the costimulatory receptor CD40 (also known as TNFRSF5) is an essential signal for the differentiation of immature DCs into fully mature DCs that are able to launch adaptive T cell-mediated immunity [5]. However, DC maturation alone does not result in a unique DC phenotype. Instead, the different signals that are provided by different microbes or viruses either directly or through the surrounding immune cells induce DCs to acquire distinct phenotypes that eventually contribute to different immune responses. Indeed, DC maturation varies according to different microbes because microbes express different pathogen associated molecular patterns (PAMPs) that trigger distinct DC molecular sensors, which are called pattern recognition receptors (PPRs). Strikingly, although most microbes activate DCs, a few can block DC maturation through various pathways [6]. Tissue-localized DCs can also be polarized into distinct phenotypes by the products released from surrounding immune cells that respond to injury. For example, gamma delta-T cells and NK cells release interferon-γ (IFNγ), mast cells release pre-formed IL-4 and TNF, pDCs secrete IFNa, stromal cells secrete IL-15 and thymic stromal lymphopoietin (TSLP), and so on. These cytokines induce the differentiation of progenitor cells or of precursor cells such as monocytes into distinct inflammatory DCs that yield unique types of T cells. On interaction of CD4 and CD8 T cells with DC, these cells can subsequently differentiate into antigen-specific effector T cells with different functions. CD4 T cells can become T helper 1 (TH1) cells, TH2 cells, TH17 cells or T follicular helper (T) cells that help B cells to differentiate into antibody-secreting cells, as well as Treg cells. Naive CD8 T cells can give rise to effector cytotoxic T lymphocytes (CTLs).

The utilization of NK cells and LAK cells in the context of cancer therapy has previously been used with success in numerous studies. Unfortunately this technology has never been commercialized in the veterinary setting. The current patent discloses specifics of utilizing a multiple canine cellular combination to stimulation cytotoxic cell production in an autologous manner.

SUMMARY

The following embodiments are provided herein:

The teachings herein are directed to methods of generating a canine immunocyte possessing cytotoxicity against cancer cells comprising: a) obtaining canine blood; b) isolating peripheral blood mononuclear cells from the canine blood; c) isolating monocytic cells from said peripheral blood mononuclear cells; d) isolating CD355+ cells from the peripheral blood mononuclear cells; e) inducing said monocytic cells to differentiate into dendritic cells; f) co-culturing said dendritic cells with said CD355+ expressing cells such that said CD355+ cells possess cytotoxicity against cancer cells.

Said peripheral blood mononuclear cells can be isolated from said canine blood by a density gradient. The density gradient can be percoll or ficoll.

Monocytic cells can be isolated by plastic adherence, magnetic activated cell separation for CD14, and fluorescent activated cell separation for CD14.

Cells expressing CD355 can be isolated by a method selected from the group consisting of: a) magnetic activated cell separation, b) fluorescent activated cell separation, and c) panning.

Monocytic cells can be differentiated into dendritic cells by culture in GM-CSF and IL-4, such as for a period of 4-8 days or 7 days. Said culture with GM-CSF and IL-4 can contain 100 IU of GM-CSF and 100 IU of IL-4.

CD355 positive cells can be cultured in IL-2 at 20 ng/ml for approximately 7 days. Canine derived dendritic cells can be co-cultured with canine derived CD355 positive cells for a period of 3 days to 30 days. The co-culture can be performed in a mixture of cytokines containing 20 ng of IL-2 per ml, and 100 IU of GM-CSF per ml.

Canine peripheral blood mononuclear cells can be cultured in a combination of 20 ng of IL-2 per ml, and 100 IU of GM-CSF per ml for a period of 7 days.

DESCRIPTION OF THE INVENTION

When practicing present invention it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To allow for the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

"antigen-presenting cells" or "APCs" are used to refer to autologous cells that express MHC Class I and/or Class II molecules that present antigens to T cells. Examples of antigen-presenting cells include, e.g., professional or non-professional antigen processing and presenting cells. Examples of professional APCs include, e.g., B cells, whole spleen cells, monocytes, macrophages, dendritic cells, fibroblasts or non-fractionated peripheral blood mononuclear cells (PMBC). Examples of hematopoietic APCs include dendritic cells, B cells and macrophages. Of course, it is understood that one of skill in the art will recognize that other antigen-presenting cells may be useful in the invention and that the invention is not limited to the exemplary cell types described herein. APCs may be "loaded" with an antigen that is pulsed, or loaded, with antigenic peptide or recombinant peptide derived from one or more antigens. In one embodiment, a peptide is the antigen and is generally antigenic fragment capable of inducing an immune response that is characterized by the activation of helper T cells, cytolytic T lymphocytes (cytolytic T cells or CTLs) that are directed against a malignancy or infection by a mammal. In one, embodiment the peptide includes one or more peptide fragments of an antigen that are presented by class I MHC or class II MHC molecules. The skilled artisan will recognize that peptides or protein fragments that are one or more fragments of other antigens may used with the present invention and that the invention is not limited to the exemplary peptides, tumor cells, cell clones, cell lines, cell supernatants, cell membranes, and/or antigens that are described herein.

"dendritic cell" or "DC" refer to all DCs useful in the present invention, that is, DC is various stages of differentiation, maturation and/or activation. In one embodiment of the present invention, the dendritic cells and responding T cells are derived from healthy volunteers. In another embodiment, the dendritic cells and T cells are derived from patients with cancer or other forms of tumor disease. In yet another embodiment, dendritic cells are used for either autologous or allogeneic application.

"effective amount" refers to a quantity of an antigen or epitope that is sufficient to induce or amplify an immune response against a tumor antigen, e.g., a tumor cell.

"vaccine" refers to compositions that affect the course of the disease by causing an effect on cells of the adaptive immune response, namely, B cells and/or T cells. The effect of vaccines can include, for example, induction of cell mediated immunity or alteration of the response of the T cell to its antigen.

"immunologically effective" refers to an amount of antigen and antigen presenting cells loaded with one or more heat-shocked and/or killed tumor cells that elicit a change in the immune response to prevent or treat a cancer. The amount of antigen-loaded and/or antigen-loaded APCs inserted or reinserted into the patient will vary between individuals depending on many factors. For example, different doses may be required for an effective immune response in a human with a solid tumor or a metastatic tumor.

"cancer cell antigen" refers to cells that have been stresses and killed in accordance with the present invention. Briefly, the cancer cells may be treated or stressed such that the cancer cell increases the expression of heat-shock proteins, such as HSP70, HSP60 and GP96, which are a class of proteins that are known to act as molecular chaperones for proteins that are or may be degraded. Generally, these heat-shock proteins will stabilize internal cancer cell antigens such that the cancer cells may include more highly immunogenic cancer cell-specific antigens.

"contacted" and "exposed", when applied to an antigen and APC, are used herein to describe the process by which an antigen is placed in direct juxtaposition with the APC. To achieve antigen presentation by the APC, the antigen is provided in an amount effective to "prime" the APCs to express antigen-loaded MHC class I and/or class II antigens on the cell surface.

"therapeutically effective amount" refers to the amount of antigen-loaded APCs that, when administered to an animal in combination, is effective to kill cancer cells within the animal. The methods and compositions of the present invention are equally suitable for killing a cancer cell or cells both in vitro and in vivo. When the cells to be killed are located within an animal, the present invention may be used in conjunction or as part of a course of treatment that may also include one or more anti-neoplastic agent, e.g., chemical, irradiation, X-rays, UV-irradiation, microwaves, electronic emissions, and the like. The skilled artisan will recognize that the present invention may be used in conjunction with therapeutically effective amount of pharmaceutical composition such a DNA damaging compound, such as, Adriamycin, 5-fluorouracil, etoposide, camptothecin, actinomycin-D, mitomycin C, cisplatin and the like. However, the present invention includes live cells that are going to activate other immune cells that may be affected by the DNA damaging agent. As such, any chemical and/or other course of treatment will generally be timed to maximize the adaptive immune response while at the same time aiding to kill as many cancer cells as possible.

"antigen-loaded dendritic cells," "antigen-pulsed dendritic cells" and the like refer to DCs that have been contacted with an antigen, in this case, cancer cells that have been heat-shocked. Often, dendritic cells require a few hours, or up to a day, to process the antigen for presentation to naive and memory T-cells. It may be desirable to pulse the DC with antigen again after a day or two in order to enhance the uptake and processing of the antigen and/or provide one or more cytokines that will change the level of maturing of the DC. Once a DC has engulfed the antigen (e.g., pre-processed heat-shocked and/or killed cancer cells), it is termed an "antigen-primed DC". Antigen-priming can be seen in DCs by immunostaining with, e.g., an antibody to the specific cancer cells used for pulsing. An antigen-loaded or pulsed DC population may be washed, concentrated, and infused directly into the patient as a type of vaccine or treatment against the pathogen or tumor cells from which the antigen originated. Generally, antigen-loaded DC are expected to interact with naive and/or memory T-lymphocytes in vivo, thus causing them to recognize and destroy cells displaying the antigen on their surfaces. In one embodiment, the antigen-loaded DC may even interact with T cells in vitro prior to reintroduction into a patient. The skilled artisan will know how to optimize the number of antigen-loaded DC per infusion, the number and the timing of infusions. For example, it will be common to infuse a patient with 1-2 million antigen-pulsed cells per infusion, but fewer cells may also induce the desired immune response.

In one embodiment the invention provides a means of generating a population of canine cells with tumoricidal ability. Peripheral blood is extracted from a canine cancer patient and peripheral blood monoclear cells (PBMC) are isolated using the Ficoll Method. PBMC are subsequently resuspended in 10 ml STEM-34 media and allowed to adhere onto a plastic surface for 2-4 hours. The adherent cells are then cultured at 37.degree. C. in STEM-34 media supplemented with 1,000 U/mL granulocyte-monocyte colony-stimulating factor and 500 U/mL IL-4 after non-adherent cells are removed by gentle washing in Hanks Buffered Saline Solution (HBSS). Half of the volume of the GM-CSF and IL-4 supplemented media is changed every other day. Immature DCs are harvested on day 7. In one embodiment said generated DC are used to stimulate T cell and NK cell tumoricidal activity. Incubation with interferon gamma may be performed for the period of 2 hours to the period of 7 days. Preferably, incubation is performed for approximately 24 hours, after which T cells and/or NK cells are stimulated via the CD3 and CD28 receptors. One means of accomplishing this is by addition of antibodies capable of activating these receptors. In one embodiment approximately, 2 ug/ml of anti-CD3 antibody is added, together with approximately 1 ug/ml anti-CD28. In order to promote survival of T cells and NK cells, was well as to stimulate proliferation, a T cell/NK mitogen may be used. In one embodiment the cytokine IL-2 is utilized. Specific concentrations of IL-2 useful for the practice of the invention are approximately 500 u/mL IL-2. Media containing IL-2 and antibodies may be changed every 48 hours for approximately 8-14 days. In one particular embodiment DC are included to said T cells and/or NK cells in order to endow cytotoxic activity towards tumor cells. In a particular embodiment, inhibitors of caspases are added in the culture so as to reduce rate of apoptosis of T cells and/or NK cells. Generated cells can be administered to a subject intradermally, intramuscularly, subcutaneously, intraperitoneally, intraarterially, intravenously (including a method performed by an indwelling catheter), intratumorally, or into an afferent lymph vessel.

In some embodiments, the culture of the cells is performed by starting with purified lymphocyte populations, for example, The step of separating the cell population and cell sub-population containing a T cell can be performed, for example, by fractionation of a mononuclear cell fraction by density gradient centrifugation, or a separation means using the surface marker of the T cell as an index. Subsequently, isolation based on surface markers may be performed. Examples of the surface marker include CD3, CD8 and CD4, and separation methods depending on these surface markers are known in the art. For example, the step can be performed by mixing a carrier such as beads or a culturing container on which an anti-CD8 antibody has been immobilized, with a cell population containing a T cell, and recovering a CD8-positive T cell bound to the carrier. As the beads on which an anti-CD8 antibody has been immobilized, for example, CD8 MicroBeads), Dynabeads M450 CD8, and Eligix anti-CD8 mAb coated nickel particles can be suitably used. This is also the same as in implementation using CD4 as an index and, for example, CD4 MicroBeads, Dynabeads M-450 CD4 can also be used. In some embodiments of the invention, T regulatory cells are depleted before initiation of the culture. Depletion of T regulatory cells may be performed by negative selection by removing cells that express makers such as neuropilin, CD25, CD4, CTLA4, and membrane bound TGF-beta. Experimentation by one of skill in the art may be performed with different culture conditions in order to generate effector lymphocytes, or cytotoxic cells, that possess both maximal activity in terms of tumor killing, as well as migration to the site of the tumor. For example, the step of culturing the cell population and cell sub-population containing a T cell can be performed by selecting suitable known culturing conditions depending on the cell population. In addition, in the step of stimulating the cell population, known proteins and chemical ingredients, etc., may be added to the medium to perform culturing. For example, cytokines, chemokines or other ingredients may be added to the medium. Herein, the cytokine is not particularly limited as far as it can act on the T cell, and examples thereof include IL-2, IFN-.gamma., transforming growth factor (TGF)-.beta., IL-15, IL-7, IFN-.alpha., IL-12, CD40L, and IL-27. From the viewpoint of enhancing cellular immunity, particularly suitably, IL-2, IFN-.gamma., or IL-12 is used and, from the viewpoint of improvement in survival of a transferred T cell in vivo, IL-7, IL-15 or IL-21 is suitably used. In addition, the chemokine is not particularly limited as far as it acts on the T cell and exhibits migration activity, and examples thereof include RANTES, CCL21, MIP1.alpha., MIP1.beta., CCL19, CXCL12, IP-10 and MIG. The stimulation of the cell population can be performed by the presence of a ligand for a molecule present on the surface of the T cell, for example, CD3, CD28, or CD44 and/or an antibody to the molecule. Further, the cell population can be stimulated by contacting with other lymphocytes such as antigen presenting cells (dendritic cell) presenting a target peptide such as a peptide derived from a cancer antigen on the surface of a cell. In addition to assessing cytotoxicity and migration as end points, it is within the scope of the current invention to optimize the cellular product based on other means of assessing T cell activity, for example, the function enhancement of the T cell in the method of the present invention can be assessed at a plurality of time points before and after each step using a cytokine assay, an antigen-specific cell assay (tetramer assay), a proliferation assay, a cytolytic cell assay, or an in vivo delayed hypersensitivity test using a recombinant tumor-associated antigen or an immunogenic fragment or an antigen-derived peptide. Examples of an additional method for measuring an increase in an immune response include a delayed hypersensitivity test, flow cytometry using a peptide major histocompatibility gene complex tetramer. a lymphocyte proliferation assay, an enzyme-linked immunosorbent assay, an enzyme-linked immunospot assay, cytokine flow cytometry, a direct cytotoxicity assay, measurement of cytokine mRNA by a quantitative reverse transcriptase polymerase chain reaction, or an assay which is currently used for measuring a T cell response such as a limiting dilution method. In vivo assessment of the efficacy of the generated cells using the invention may be assessed in a living body before first administration of the T cell with enhanced function of the present invention, or at various time points after initiation of treatment, using an antigen-specific cell assay, a proliferation assay, a cytolytic cell assay, or an in vivo delayed hypersensitivity test using a recombinant tumor-associated antigen or an immunogenic fragment or an antigen-derived peptide. Examples of an additional method for measuring an increase in an immune response include a delayed hypersensitivity test, flow cytometry using a peptide major histocompatibility gene complex tetramer. a lymphocyte proliferation assay, an enzyme-linked immunosorbent assay, an enzyme-linked immunospot assay, cytokine flow cytometry, a direct cytotoxicity assay, measurement of cytokine mRNA by a quantitative reverse transcriptase polymerase chain reaction, or an assay which is currently used for measuring a T cell response such as a limiting dilution method. Further, an immune response can be assessed by a weight, diameter or malignant degree of a tumor possessed by a living body, or the survival rate or survival term of a subject or group of subjects.

In one embodiment of the invention water-soluble acidic peptidoglycan from sprouts of the plant *Solanum tuberosum* (WSPG) as described in Russian Patent RU 2195308 is utilized to generate ex vivo cytolytic canine lymphocytes by culture with canine lymphocytes. WSPG is a highly effective and non-toxic immunomodulator capable to activate immune cells to fight metastatic cancer. WSPG simultaneously activates several types of antitumor immune cells, particularly WSPG converts DC to tumor killer cells, causes the production of cytokines by dendritic cells, activating NK cells which enhances their cytotoxic activity against tumor; also under influence of WSPG occurs reprogramming of macrophages into tumor killers, even tumor-associated macrophages are transformed into macrophages that actively kill various tumors.

In one embodiment of the invention, ascorbic acid is administered intravenously together with activated lymphocytes which possess tumor inhibitory/killing activity. In a preferred embodiment the intravenous vitamin C is administered once every two days at a concentration of 10 g per injection. The rational for use of intravenous vitamin C comes from observations of a scurvy-like condition in a renal cell carcinoma patient treated with IL-2. The patient presented with acute signs and symptoms of scurvy (perifollicular petechiae, erythema, gingivitis and bleeding). Serum ascorbate levels were significantly reduced to almost undetectable levels [24]. Although the role of ascorbic acid (AA) hypersupplementation in stimulation of immunity in healthy subjects is controversial, it is well established that AA deficiency is associated with impaired cell mediated immunity. This has been demonstrated in numerous studies showing deficiency suppresses T cytotoxic responses, delayed type hypersensitivity, and bacterial clearance [25]. Additionally, it is well-known that NK activity, which IL-2 is anti-tumor activity is highly dependent on, is suppressed during conditions of AA deficiency [26]. Thus it may be that while IL-2 therapy on the one hand is stimulating T and NK function, the systemic inflammatory syndrome-like effects of this treatment may actually be suppressed by induction of a negative feedback loop. Such a negative feedback loop with IL-2 therapy was successfully overcome by work using low dose histamine to inhibit IL-2 mediated immune suppression, which led to the "drug" Ceplene (histamine dichloride) receiving approval as an IL-2 adjuvant for treatment of AML [27].

The antigen-loaded DCs may be co-cultured with T-lymphocytes to produce antigen-specific T-cells. As used herein, the term "antigen-specific T-cells" refers to T-cells that proliferate upon exposure to the antigen-loaded APCs of the present invention, as well as to develop the ability to attack cells having the specific antigen on their surfaces. Such T-cells, e.g., cytotoxic T-cells, lyse target cells by a number of methods, e.g., releasing toxic enzymes such as granzymes and perform onto the surface of the target cells or by effecting the entrance of these lytic enzymes into the target cell interior. Generally, cytotoxic T-cells express CD8 on their cell surface. T-cells that express the CD4 antigen CD4, commonly known as "helper" T-cells, can also help promote specific cytotoxic activity and may also be activated by the antigen-loaded APCs of the present invention. In certain embodiments, the cancer cells, the APCs and even the T-cells can be derived from the same donor whose MNC yielded the DC, which can be the patient or an HLA—or obtained from the individual patient that is going to be treated. Alternatively, the cancer cells, the APCs and/or the T-cells can be allogeneic.

The invention provides means of inducing an anti-cancer response in a mammal, comprising the steps of initially "priming" the mammal by administering an agent that causes local accumulation of antigen presenting cells. Subsequently, a tumor antigen is administered in the local area where said agents causing accumulation of antigen presenting cells is administered. A time period is allowed to pass to allow for said antigen presenting cells to traffic to the lymph nodes. Subsequently a maturation signal, or a plurality of maturation signals are administered to enhance the ability of said antigen presenting cell to activate adaptive immunity. In some embodiments of the invention activators of adaptive immunity are concurrently given, as well as inhibitors of the tumor derived inhibitors are administered to derepress the immune system.

In one embodiment priming of the patient is achieved by administration of GM-CSF subcutaneously in the area in which antigen is to be injected. Various scenarios are known in the art for administration of GM-CSF prior to administration, or concurrently with administration of antigen. The practitioner of the invention is referred to the following publications for dosage regimens of GM-CSF and also of peptide antigens [7-18]. Subsequent to priming, the invention calls for administration of tumor antigen. Various tumor antigens may be utilized, in one preferred embodiment, lysed tumor cells from the same patient area utilized. Means for generation of lyzed tumor cells are well known in the art and described in the following references [19-25]. One example method for generation of tumor lysate involves obtaining frozen autologous samples which are placed in hanks buffered saline solution (HBSS) and gentamycin 50 µg/ml followed by homogenization by a glass homogenizer. After repeated freezing and thawing, particle-containing samples are selected and frozen in aliquots after radiation with 25 kGy. Quality assessment for sterility and endotoxin content is performed before freezing. Cell lysates are subsequently administered into the patient in a preferred manner subcutaneously at the local areas where DC priming was initiated. After 12-72 hours, the patient is subsequently administered with an agent capable of inducing maturation of DC. Agents useful for the practice of the invention, in a preferred embodiment include BCG and HMGB1 peptide. Other useful agents include: a) histone DNA; b) imiqimod; c) beta-glucan; d) hsp65; e) hsp90; f) HMGB-1; g) lipopolysaccharide; h) Pam3CSK4; i) Poly I: Poly C; j) Flagellin; k) MALP-2; l) Imidazoquinoline; m) Resiquimod; n) CpG oligonucleotides; o) zymosan; p) peptidoglycan; q) lipoteichoic acid; r) lipoprotein from gram-positive bacteria; s) lipoarabinomannan from mycobacteria; t) Polyadenylic-polyuridylic acid; u) monophosphoryl lipid A; v) single stranded RNA; w) double stranded RNA; x) 852A; y) rintatolimod; z) Gardiquimod; and aa) lipopolysaccharide peptides. The procedure is performed in a preferred embodiment with the administration of IDO silencing siRNA or shRNA. siRNA or shRNA may be administered through various modalities including biodegradable matrices, pressure gradients or viral transfect. In another embodiment, autologous dendritic cells are generated and IDO is silenced, prior to, concurrent with or subsequent to silencing, said dendritic cells are pulsed with tumor antigen and administered systemically.

Culture of dendritic cells is well known in the art, for example, U.S. Pat. No. 6,936,468, issued to Robbins, et al., for the use of tolerogenic dendritic cells for enhancing tolerogenicity in a host and methods for making the same. Although the current invention aims to reduce tolerogenesis, the essential means of dendritic cell generation are disclosed in the patent. U.S. Pat. No. 6,734,014, issued to Hwu, et al., for methods and compositions for transforming dendritic cells and activating T cells. Briefly, recombinant dendritic cells are made by transforming a stem cell and differentiating the stem cell into a dendritic cell. The resulting dendritic cell is said to be an antigen presenting cell which activates T cells against MHC class I-antigen targets. Antigens for use in dendritic cell loading are taught in, e.g., U.S. Pat. No. 6,602,709, issued to Albert, et al. This patent teaches methods for use of apoptotic cells to deliver antigen to dendritic cells for induction or tolerization of T cells. The methods and compositions are said to be useful for delivering antigens to dendritic cells that are useful for inducing antigen-specific cytotoxic T lymphocytes and T helper cells. The disclosure includes assays for evaluating the activity of cytotoxic T lymphocytes. The antigens targeted to dendritic cells are apoptotic cells that may also be modified to express non-native antigens for presentation to the dendritic cells. The dendritic cells are said to be primed by the apoptotic cells (and fragments thereof) capable of processing and presenting the processed antigen and inducing cytotoxic T lymphocyte activity or may also be used in vaccine therapies. U.S. Pat. No. 6,455,299, issued to Steinman, et al., teaches methods of use for viral vectors to deliver antigen to dendritic cells. Methods and compositions are said to be useful for delivering antigens to dendritic cells, which are then useful for inducing T antigen specific cytotoxic T lymphocytes. The disclosure provides assays for evaluating the activity of cytotoxic T lymphocytes. Antigens are provided to dendritic cells using a viral vector such as influenza virus that may be modified to express non-native antigens for presentation to the dendritic cells. The dendritic cells are infected with the vector and are said to be capable of presenting the antigen and inducing cytotoxic T lymphocyte activity or may also be used as vaccines.

One skilled in the art will appreciate that these methods and devices are and can be adapted to carry out the objects and obtain the ends and advantages mentioned, as well as those inherent therein. The methods, procedures, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure.

It is apparent to one skilled in the art that varying substitutions and modifications can be made to the invention disclosed herein without departing from the scope and spirit of the invention. Furthermore, those skilled in the art recognize that the aspects and embodiments of the invention set forth herein can be practiced separate from each other or in conjunction with each other. Therefore, combinations of separate embodiments are within the scope of the invention as disclosed herein.

REFERENCES

1. Steinman, R. M. and Z. A. Cohn, *Identification of a novel cell type in peripheral lymphoid organs of mice. I. Morphology, quantitation, tissue distribution*. J Exp Med, 1973. 137(5): p. 1142-62.
2. Banchereau, J. and R. M. Steinman, *Dendritic cells and the control of immunity*. Nature, 1998. 392(6673): p. 245-52.
3. Trombetta, E. S. and I. Mellman, *Cell biology of antigen processing in vitro and in vivo*. Annu Rev Immunol, 2005. 23: p. 975-1028.
4. Itano, A. A. and M. K. Jenkins, *Antigen presentation to naive CD4 T cells in the lymph node*. Nat Immunol, 2003. 4(8): p. 733-9.
5. Caux, C., et al., *Activation of human dendritic cells through CD40 cross-linking*. J Exp Med, 1994. 180(4): p. 1263-72.
6. Pulendran, B., K. Palucka, and J. Banchereau, *Sensing pathogens and tuning immune responses*. Science, 2001. 293(5528): p. 253-6.
7. Middleton, G., et al., *Gemcitabine and capecitabine with or without telomerase peptide vaccine GV1001 in patients with locally advanced or metastatic pancreatic cancer (TeloVac): an open-label, randomised, phase 3 trial*. Lancet Oncol, 2014. 15(8): p. 829-40.
8. Mittendorf, E. A., et al., *Final report of the phase I/II clinical trial of the E75 (nelipepimut-S) vaccine with booster inoculations to prevent disease recurrence in high-risk breast cancer patients*. Ann Oncol, 2014. 25(9): p. 1735-42.
9. Rahma, O. E., et al., *The immunological and clinical effects of mutated ras peptide vaccine in combination with IL-2, GM-CSF, or both in patients with solid tumors*. J Transl Med, 2014. 12: p. 55.
10. Clancy-Thompson, E., et al., *Peptide vaccination in Montanide adjuvant induces and GM-CSF increases CXCR3 and cutaneous lymphocyte antigen expression by tumor antigen-specific CD8 T cells*. Cancer Immunol Res, 2013. 1(5): p. 332-9.
11. Sonpavde, G., et al., *HLA-restricted NY-ESO-1 peptide immunotherapy for metastatic castration resistant prostate cancer*. Invest New Drugs, 2014. 32(2): p. 235-42.
12. Geynisman, D. M., et al., *A randomized pilot phase I study of modified carcinoembryonic antigen (CEA) peptide (CAP1-6D)/montanide/GM-CSF-vaccine in patients with pancreatic adenocarcinoma*. J Immunother Cancer, 2013. 1: p. 8.
13. Tarhini, A. A., et al., *Differing patterns of circulating regulatory T cells and myeloid-derived suppressor cells in metastatic melanoma patients receiving anti-CTLA4 anti-* body and intelferon-alpha or TLR-9 agonist and GM-CSF with peptide vaccination. J Immunother, 2012. 35(9): p. 702-10.
14. Walter, S., et al., *Multipeptide immune response to cancer vaccine IMA901 after single-dose cyclophosphamide associates with longer patient survival.* Nat Med, 2012. 18(8): p. 1254-61.
15. Ohno, S., et al., *Phase I trial of Wilms' Tumor 1 (WT1) peptide vaccine with GM-CSF or CpG in patients with solid malignancy.* Anticancer Res, 2012. 32(6): p. 2263-9.
16. Tarhini, A. A., et al., *Safety and immunogenicity of vaccination with MART-1 (26-35, 27L), gp100 (209-217, 210M), and tyrosinase (368-376, 370D) in adjuvant with PF-3512676 and GM-CSF in metastatic melanoma.* J Immunother, 2012. 35(4): p. 359-66.
17. Schaefer, C., et al., *Function but not phenotype of melanoma peptide-specific CD8(+) T cells correlate with survival in a multiepitope peptide vaccine trial (ECOG 1696).* Int J Cancer, 2012. 131(4): p. 874-84.
18. Block, M. S., et al., *Pilot study of granulocyte-macrophage colony-stimulating factor and interleukin-2 as immune adjuvants for a melanoma peptide vaccine.* Melanoma Res, 2011. 21(5): p. 438-45.
19. Bapsy, P. P., et al., *Open-label, multi-center, non-randomized, single-arm study to evaluate the safety and efficacy of dendritic cell immunotherapy in patients with refractory solid malignancies, on supportive care.* Cytotherapy, 2014. 16(2): p. 234-44.
20. Reyes, D., et al., *Tumour cell lysate-loaded dendritic cell vaccine induces biochemical and memory immune response in castration-resistant prostate cancer patients.* Br J Cancer, 2013. 109(6): p. 1488-97.
21. Kamigaki, T., et al., *Immunotherapy of autologous tumor lysate-loaded dendritic cell vaccines by a closed-flow electroporation system for solid tumors.* Anticancer Res, 2013. 33(7): p. 2971-6.
22. Florcken, A., et al., *Allogeneic partially HLA-matched dendritic cells pulsed with autologous tumor cell lysate as a vaccine in metastatic renal cell cancer: a clinical phase I/II study.* Hum Vaccin Immunother, 2013. 9(6): p. 1217-27.
23. Cho, D. Y., et al., *Adjuvant immunotherapy with whole-cell lysate dendritic cells vaccine for glioblastoma multiforme: a phase II clinical trial.* World Neurosurg, 2012. 77(5-6): p. 736-44.
24. Alfaro, C., et al., *Pilot clinical trial of type 1 dendritic cells loaded with autologous tumor lysates combined with GM-CSF, pegylated IFN, and cyclophosphamide for metastatic cancer patients.* J Immunol, 2011. 187(11): p. 6130-42.
25. Fadul, C. E., et al., *Immune response in patients with newly diagnosed glioblastoma multiforme treated with intranodal autologous tumor lysate-dendritic cell vaccination after radiation chemotherapy.* J Immunother, 2011. 34(4): p. 382-9.

The invention claimed is:

1. A method of inducing cytotoxicity against cancer cells in CD355+ lymphocytes comprising: a) obtaining canine blood; b) isolating peripheral blood mononuclear cells from the canine blood; c) isolating monocytic cells from said peripheral blood mononuclear cells; d) isolating CD355+ lymphocyte cells from the peripheral blood mononuclear cells; e) inducing said monocytic cells to differentiate into dendritic cells; f) co-culturing said dendritic cells with said CD355+ expressing lymphocyte cells such that said CD355+ lymphocyte cells possess cytotoxicity against cancer cells.

2. The method of claim 1, wherein said peripheral blood mononuclear cells are isolated from said canine blood by a density gradient.

3. The method of claim 2, wherein said density gradient is percoll.

4. The method of claim 2, wherein said density gradient is ficoll.

5. The method of claim 1, wherein said monocytic cells are isolated by plastic adherence.

6. The method of claim 1, wherein said monocytic cells are isolated by magnetic activated cell separation for CD14.

7. The method of claim 1, wherein said monocytic cells are isolated by fluorescent activated cell separation for CD14.

8. The method of claim 1, wherein said lymphocyte cells expressing CD355 are isolated by a method selected from the group consisting of: a) magnetic activated cell separation, and b) fluorescent activated cell separation.

9. The method of claim 1, wherein said monocytic cells are differentiated into dendritic cells by culture in GM-CSF and IL-4.

10. The method of claim 9, wherein said culture with GM-CSF and IL-4 is for a period of 4-8 days.

11. The method of claim 10, wherein said culture with GM-CSF and IL-4 is for a period of 7 days.

12. The method of claim 11, wherein said culture with GM-CSF and IL-4 contains 100 IU of GM-CSF and 100 IU of IL-4.

13. The method of claim 1, wherein said CD355 positive lymphocyte cells are cultured in IL-2 at 20 ng/ml for approximately 7 days.

14. The method of claim 13, wherein said canine derived dendritic cells are co-cultured with canine derived CD355 positive lymphocyte cells for a period of 3 days to 30 days.

15. The method of claim 14, wherein said co-culture is performed in a mixture of cytokines containing 20 ng of IL-2 per ml, and 100 IU of GM-CSF per ml.

16. The method of claim 1, wherein canine peripheral blood mononuclear cells are cultured in a combination of 20 ng of IL-2 per ml, and 100 IU of GM-CSF per ml for a period of 7 days.

* * * * *